United States Patent
Hottinger et al.

(10) Patent No.: US 8,721,697 B2
(45) Date of Patent: *May 13, 2014

(54) HANDPIECE WITH CARTRIDGE FOR A SKIN PHOTO-TREATMENT APPARATUS

(75) Inventors: Christophe Hottinger, Paris (FR); Pascale Tannous, Paris (FR)

(73) Assignee: Dermeo, Paris (FR)

( * ) Notice: Subject to any disclaimer, the term of this patent is extended or adjusted under 35 U.S.C. 154(b) by 169 days.

This patent is subject to a terminal disclaimer.

(21) Appl. No.: 13/063,447

(22) PCT Filed: Sep. 11, 2009

(86) PCT No.: PCT/FR2009/051712
§ 371 (c)(1),
(2), (4) Date: May 20, 2011

(87) PCT Pub. No.: WO2010/031947
PCT Pub. Date: Mar. 25, 2010

(65) Prior Publication Data
US 2011/0238142 A1   Sep. 29, 2011

(30) Foreign Application Priority Data
Sep. 16, 2008  (FR) ...................................... 08 56204
Sep. 9, 2009   (FR) ...................................... 09 56126

(51) Int. Cl.
*A61N 5/06*   (2006.01)
(52) U.S. Cl.
USPC ............................................ 607/90; 607/91

(58) Field of Classification Search
USPC .............. 607/88–91; 606/1, 9, 10, 13, 16–18, 606/20–23
See application file for complete search history.

(56) References Cited

U.S. PATENT DOCUMENTS

| 2007/0198004 A1 | 8/2007 | Altshuler |
| 2011/0213447 A1* | 9/2011 | Hottinger et al. ............... 607/90 |

FOREIGN PATENT DOCUMENTS

| EP | 1535582 A | 6/2005 |
| EP | WO2008/088792 A | 6/2005 |
| WO | WO03/043514 A | 5/2003 |
| WO | WO2007/007167 A | 1/2007 |
| WO | WO2008/012519 A | 1/2008 |
| WO | WO2008/070747 A | 6/2008 |
| WO | WO2008/088795 A | 7/2008 |

* cited by examiner

*Primary Examiner* — Ahmed Farah
(74) *Attorney, Agent, or Firm* — Drinker, Biddle & Reath, LLP

(57) ABSTRACT

A handpiece having a shell for removably housing a cartridge with a window having a light source and a cooling circuit thereof as well as a cover. A light guide connects the light source to the surface of the skin. The position of the cartridge is defined by a base having cartridge connection members and by a guiding surface having one end corresponding to the base and sides defining lateral guide rails around the position of the light guide. The cartridge is in the form of a planar housing having one end bearing a transverse assembly plate provided with connection members homologous to those of the base, and the sides include guiding ribs interacting with the lateral rails.

9 Claims, 6 Drawing Sheets

HANDPIECE WITH CARTRIDGE FOR A SKIN PHOTO-TREATMENT APPARATUS

FIELD OF THE INVENTION

Figure 1:
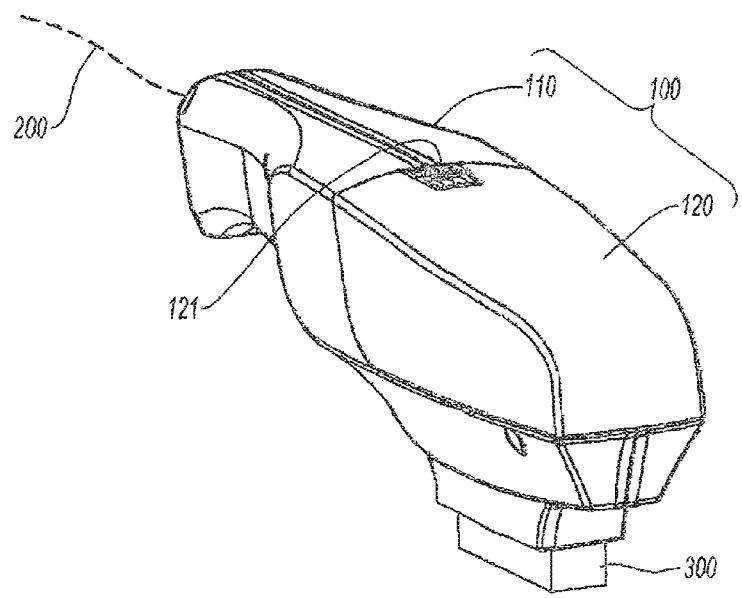

The present invention relates to a handpiece for a cosmetic, medical/therapeutic skin phototreatment device, which handpiece is connected to a power and liquid coolant supply unit by a cable and tube connection in the device and comprises
- a shell which houses, in a removable manner, a cartridge with a window having a light source and its cooling circuit and a cap which closes the site of the cartridge in the shell,
- a light guide which is connected to the light source by the window of the cartridge and the outlet surface of which is to be applied to or above the surface of the skin to be treated.

PRIOR ART

Various types of handpieces for such devices are known. Such handpieces house the controlled light source as well as the light guide which transmits the light from the source to the outlet surface of the handpiece, which is positioned above or in contact with the skin, for example according to document WO 02/08 2866.

It is also known according to document EP 1 535 582 to produce a handpiece for a cosmetic, medical/therapeutic skin phototreatment device having a removable part, which is fixed by screwing. The movable part is composed not only of the cartridge but also of the optical assembly downstream thereof. It is a casing having an outlet window and a part for preventing direct contact between the filter and the skin. The assembly slides in rails in an opening formed in the bottom of the handle. However, in that document there is no base above the light guide and the cartridge connection members, which would be connected to the base, because the assembly slides in the handle.

According to document WO 2008/088792 there is produced a handpiece whose optical outlet is constituted by a fibre-optic brush so as to channel the light flux onto the punctual surfaces at the outlet of the optical fibres.

The part composed of the bundle of optical fibres and of the support which guides the fibres towards rods constituting light guides, and which are parallel in order to provide light spots, is detachable. However, it is not a cartridge within the meaning of the present invention, nor is the optical part of the device removable, the structure of the optical part being completely different from that of the present invention, the optical part being composed especially of a reflecting mirror and an objective lens for concentrating the light beam on the inlet surface constituted by the concentration of the ends of the optical fibres.

According to document WO 2008/070747 there is known another type of handpiece for a skin phototreatment device. That device comprises different optical heads, but there is no mention of the interchangeability of the cartridge constituting the light source.

It is also known, according to document WO 03/043514, to produce a device handpiece in which the whole of the optical part can be removed from the handpiece. The optical part constitutes a unit. It is not the lamp emitting the flashes but the whole of the power supply and operating control system of the lamp.

According to document WO 2008/012519 there also exists a cartridge constituting a pulsed light source provided with electric and hydraulic connection means for supplying power to and cooling the lamp. However, it is a simple plug-in connection without guide and positioning means other than for the cartridge comprising the lamp.

A cartridge for a handpiece is known from document WO 07/007,167.

The disadvantage of that cartridge is its retention and its connection, both electrical and fluidic, with the complementary elements of the handpiece. This creates problems of leakage or electrical contact which reduce the life of the lamp.

In greater detail, the manner in which the cartridge is connected is inadequate; there is a risk of its becoming disconnected under the effect of the flashes, which create vibrations. Those vibrations also create risks of leaks and breaks of the electrical connections.

The cartridge is poorly retained so that it is unable to supply the light energy correctly because of poor contact with the light guide. That poor retention also risks damaging the connectors.

The cartridge requires a temperature sensor to avoid a rise in temperature above a critical threshold in order to avoid injuring the patient by an excessive rise in the temperature of the equipment, which would risk burning the patient.

OBJECT OF THE INVENTION

It is an object of the present invention to develop a handpiece for a cosmetic, medical/therapeutic skin phototreatment device which allows the cartridge containing the light source to be replaced easily, providing better tightness for the fluidic connection and better contact in order to improve the life of the cartridge and facilitate its fitting and use while avoiding interruptions in operation associated with possible overheating.

DESCRIPTION AND ADVANTAGES OF THE INVENTION

To that end, the invention relates to a handpiece of the type defined above, characterised in that
- the site of the cartridge above the light guide is defined by a base carrying the connection members for the cartridge and by a guide surface, one end of which corresponds to the base and the sides of which are lateral guide rails around the site of the light guide, and
- the cartridge is in the form of a planar casing, one end of which carries a transverse assembly plate provided with connection members homologous to those of the base, and the sides of which comprise guide ribs for cooperating with the lateral rails of the site, positioning the cartridge and guiding it in its translational movement towards its site for insertion and connection at the end of its travel, and for keeping it connected.

The cartridge of this handpiece is easily accessible and it is removed by a simple translational movement. The cartridge is nevertheless held firmly in its site owing to the guide rails, which keep the cartridge pressed against its site and against the base, avoiding any risk of disconnection.

According to another advantageous feature,
- at the site of the cartridge the shell comprises additional rails parallel to those which are to guide the cartridge, as well as a clip-fit element,
- the cap which covers the site of the cartridge and completes the shell comprises guide members for sliding in the additional rails, as well as a complementary clip-fit element for cooperating with the clip-fit element of the shell when the cap is in the closed position.

The cap covering the site of the cartridge, which is fitted by sliding and then locking by means of a clip-fit element, secures the cap and, consequently, completes the holding of the cartridge in its site.

Advantageously, the cap comprises on the inside a flexible stop which presses against the front end of the cartridge and completes the holding thereof, which is already ensured by the ribs and the rails and the engagement of the connection members in the base. The cartridge is thus held perfectly in its site for correct transmission of the light flux injected by the light source into the light guide.

According to another feature, the casing of the cartridge comprises two lateral grip zones which allow the casing to be grasped by hand or withdrawn and inserted by a sliding movement of its ribs in the rails.

This particular form of the casing facilitates the removal of the cartridge or its insertion, without having to grasp the cartridge too tightly.

Finally, the two lateral grip zones constitute grip surfaces which encourage the user to hold the cartridge in those zones in order to prevent his fingers from coming into contact with the window of the light source of the cartridge. This is particularly important when the cartridge is taken out of the shell and is in any orientation.

When the cartridge is inserted in the base of the shell, the window of the cartridge naturally faces the light guide while the hand comes into contact with the other face of the cartridge in order to grasp it by the two lateral grip zones.

According to another advantageous feature,
the casing of the cartridge is formed of two parts which house the light source and its liquid coolant circuit,
one of the parts has a window in which the light source appears in order to transmit its light flux,
the two parts being assembled along a joining plane which is substantially parallel to the plane of the site,
the lower part carries the ribs, and its end carries the assembly plate.

The casing has a form which is simple to produce despite the complexity of the elements constituting the casing of the cartridge and, in particular, the liquid coolant circuit.

The shell is advantageously so produced that it is composed of two parts, which meet substantially in the mid-plane, and of the cap above the site of the cartridge, as well as of housings for receiving the base for the connection of the cartridge.

Advantageously, the cap comprises a fan beneath its upper wall, which is provided with ventilation orifices, and above the site of the cartridge,
the shell having in its lateral walls, on either side of the cartridge, ventilation slots for the exit of air,
an air passage path being formed between the orifices in the top of the cap, through the fan and the top of the cartridge, dividing towards the sides of the cartridge and emerging through the ventilation slots of the shell next to the cartridge.

The forced ventilation of the enclosure of the handle, delimited by the shell and the cap enclosing the cartridge, prevents overheating of the enclosure and ill-timed interruptions in operation, which would require the device to be out of use for a more or less prolonged period.

Integration of the fan in the handpiece is particularly simple because the fan is associated with the cap and not with the shell. This simplifies manufacture of the moulds used to produce the handpiece.

According to an advantageous feature, the cap comprises two pins for supplying power to the motor of the fan, which pins engage in sockets in the shell next to the locking hook.

This method of supplying power to the fan of the cap facilitates operations inside the enclosure, that is to say, for example, the replacement of the cartridge without having to dismantle the supply to the fan because connection is effected automatically by the fitting of the cap, all the more so since, according to the invention, the cap slides into the assembly position in a rail of the cap, the final phase being carried out by engaging the hook of the cap in a corresponding housing in the cap.

According to another feature, a control circuit for the operation of the fan (operating speed/flow rate) is connected to a temperature sensor associated with the enclosure of the handle (shell and cap) in order to control the operation of the fan as a function of the temperature detected inside the enclosure of the handpiece.

This mode of operation is adapted to the intensity of use of the handpiece, avoiding running the motor of the fan excessively.

Furthermore, relative to the prior art, since the forced airflow enters at the top of the cartridge, at the hottest point thereof because it is located behind the discharge lamp, a temperature that causes an interruption in the operation of the machine is never reached. This thus avoids the recovery period which, according to the prior art, can be very long because, if the temperature permitted for operation is exceeded, the machine stops and cannot begin to operate again until the temperature falls below the limit. However, the situation is then precarious because the temperature very quickly exceeds the limit again and the device stops once more. This intermittent operation of the known installations is avoided completely by the forced airflow and the resulting cooling of the enclosure of the handpiece.

According to another advantageous feature, the casing of the fan is clipped into retaining tabs moulded in one piece with the cap.

This embodiment is of interest for the moulding of the piece, that is to say of the cap; insertion of the fan is carried out under particularly simple conditions. After insertion, the two power supply leads simply have to be welded to the pins integrated into the cap of the handpiece, for example at the time of injection moulding of the handpiece.

DRAWINGS

Figure 2:
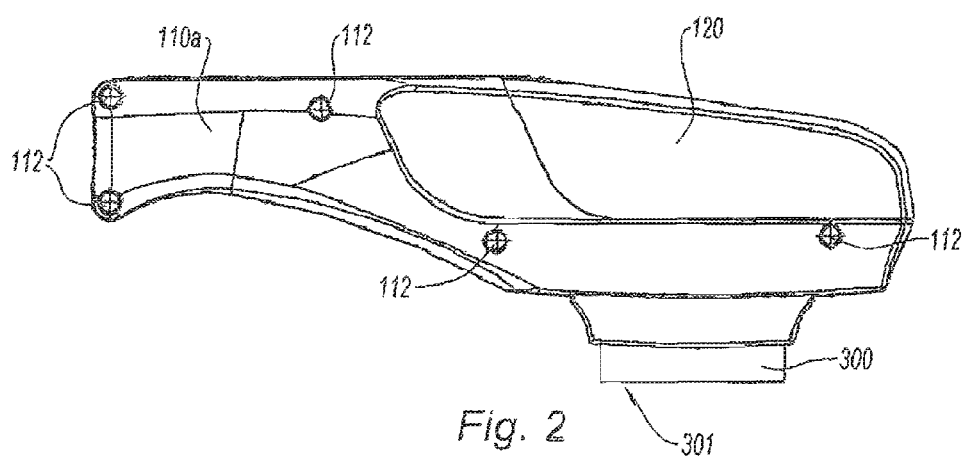
Figure 3:
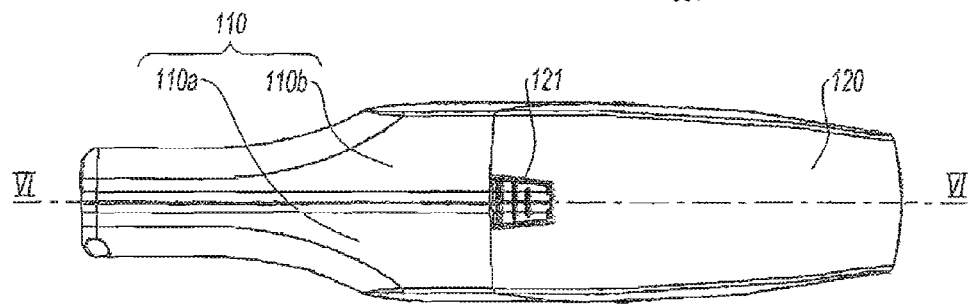
Figure 4:
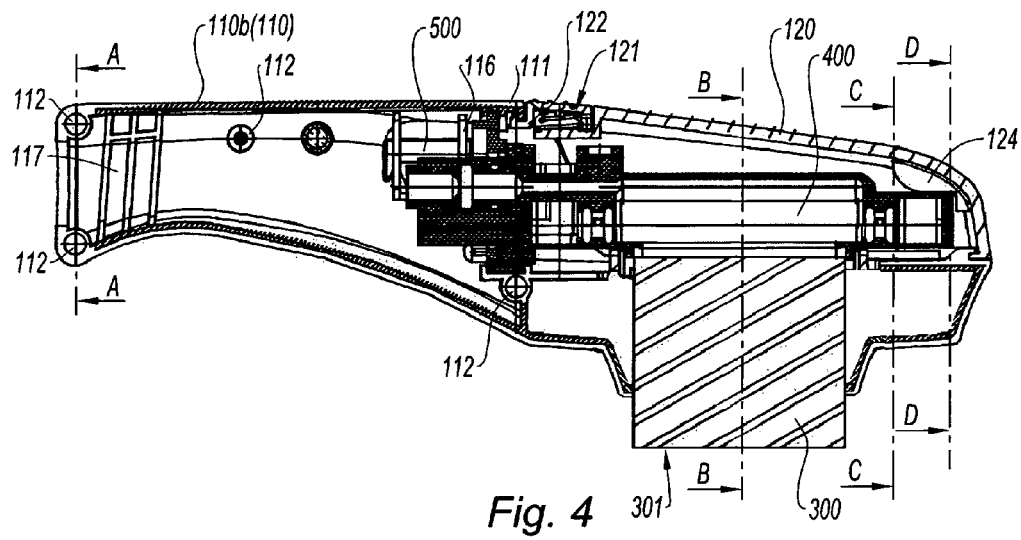
Figure 5A:
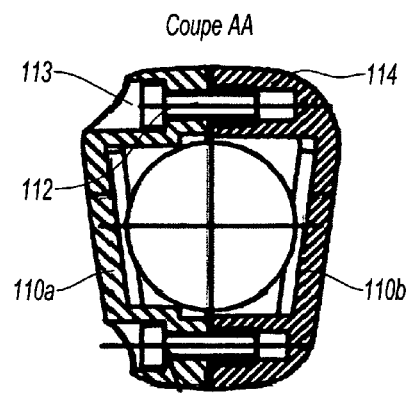
Figure 5B:
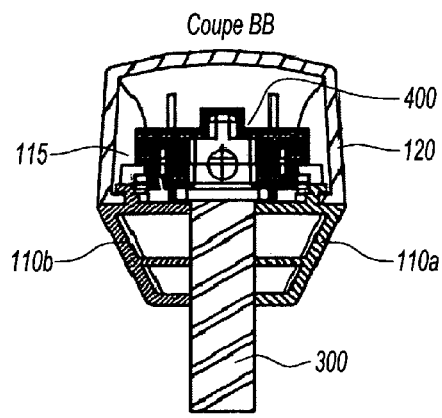
Figure 5C:
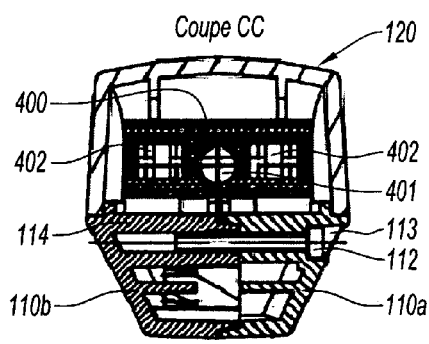
Figure 5D:
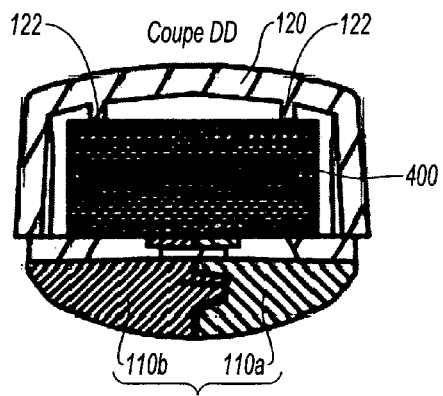
Figure 6:
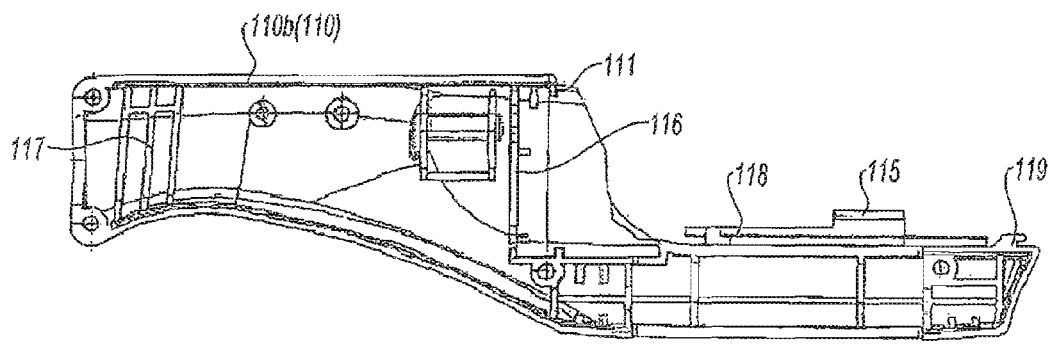
Figure 7:
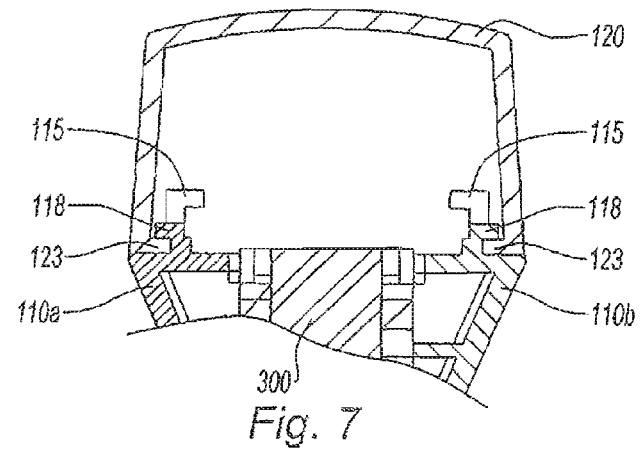
Figure 8:
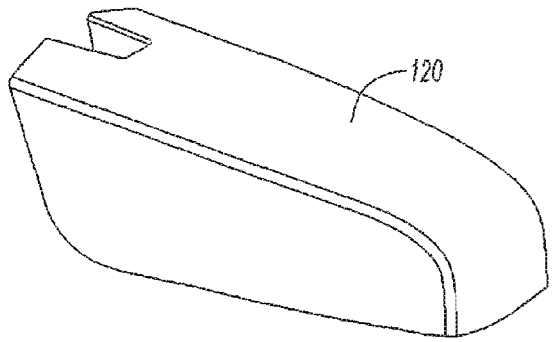
Figure 9:
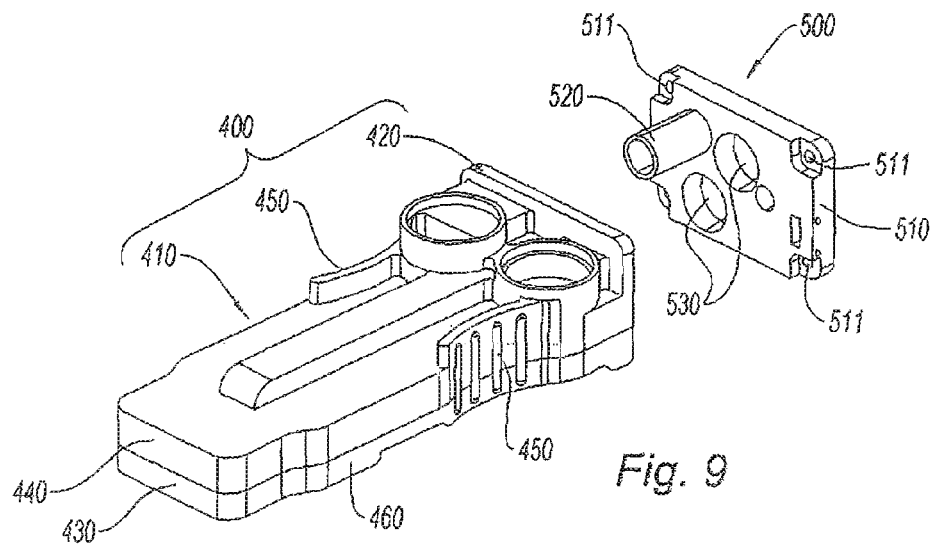
Figure 10A:
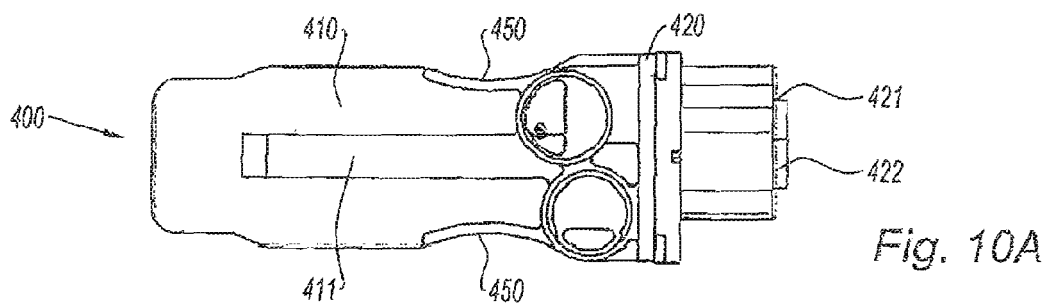
Figure 10B:
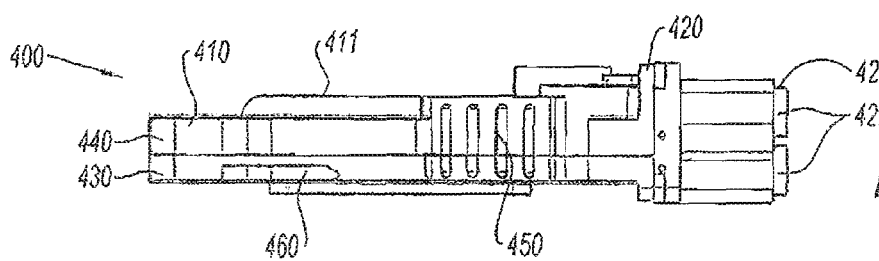
Figure 10C:
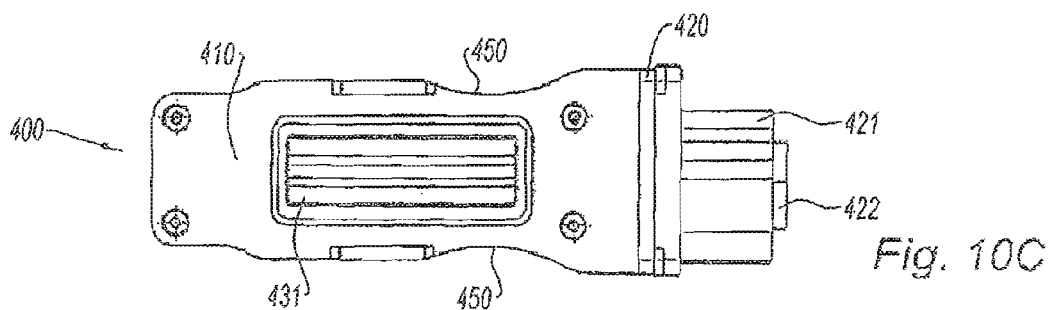
Figure 11:
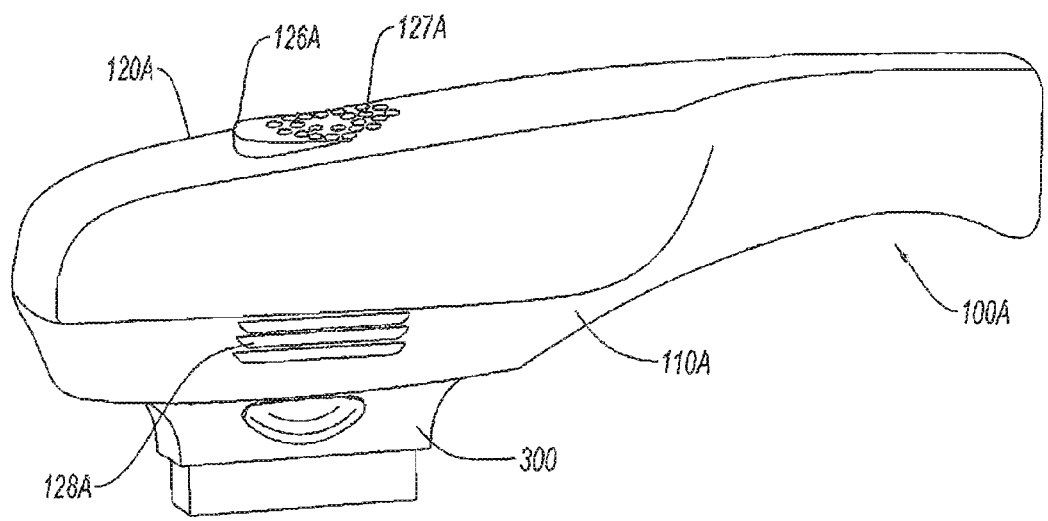
Figure 12:
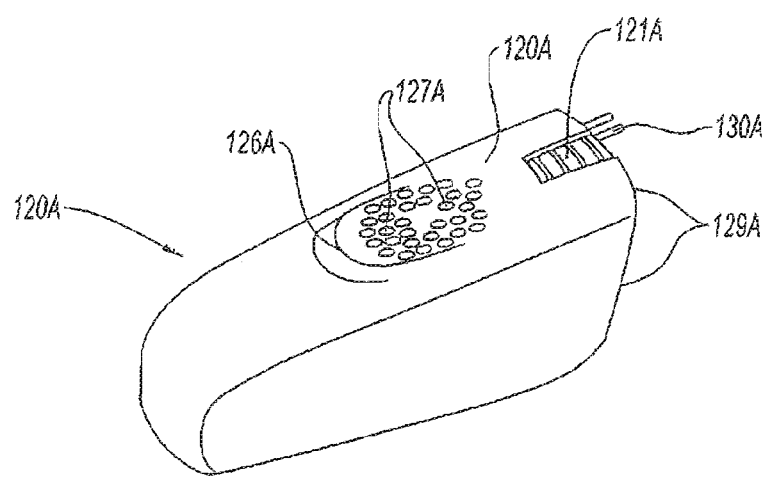
Figure 13:
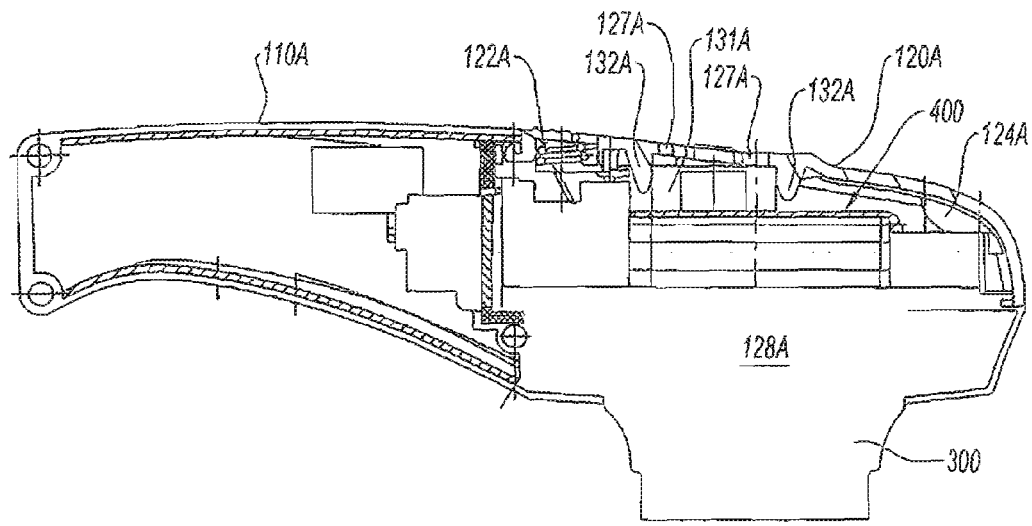
Figure 14:
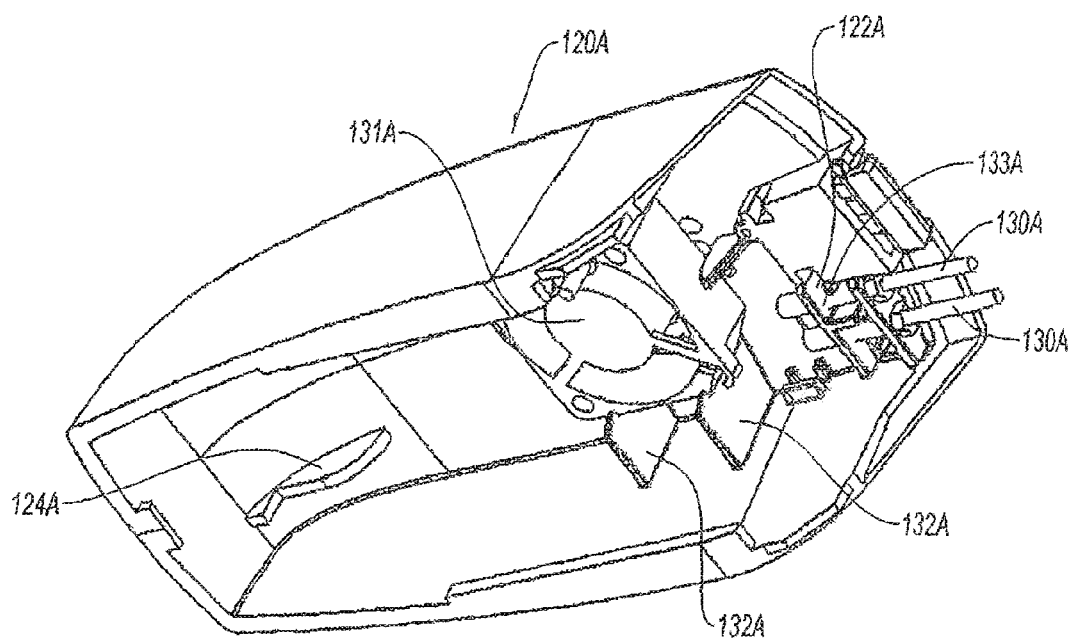

The present invention will be described in greater detail hereinbelow with the aid of an exemplary embodiment of a handpiece shown diagrammatically in the accompanying drawings, in which:

FIG. 1 is an isometric view of an embodiment of the handpiece,

FIGS. 2 and 3 show a side view and a top view, respectively, of the handpiece of FIG. 1, FIG. 4 is a sectional view through a mid-plane of the handpiece of FIG. 1, FIGS. 5A to 5D are sectional views according to cutting planes A, B, C, D of FIG. 4, FIG. 6 is a sectional view according to plane VI VI of FIG. 3, FIG. 7 is a sectional view according to plane BB of FIG. 4 on an enlarged scale and without the cartridge, FIG. 8 is an isometric view of the cap of the shell, FIG. 9 is an isometric view of the cartridge and of the base aligned for the purposes of connection, FIG. 10A is a top view of the cartridge of FIG. 9, FIG. 10B is a side view of the cartridge of FIG. 9, FIG. 10C is a bottom view of the cartridge of FIG. 9, FIG. 11 is a perspective view of a variant of a handpiece according to the invention, FIG. 12 is a perspective view of the cap of the handpiece of FIG. 11, FIG. 13 is a partial longitudinal sectional view showing the modified part of the handpiece according to that variant, FIG. 14 is a perspective bottom view of the cap of the handpiece.

DESCRIPTION OF AN EMBODIMENT

According to FIGS. 1, 2 and 3, the invention relates to a handpiece for a cosmetic, medical or therapeutic skin phototreatment device. The handpiece 100 is connected by fluidic and electrical connections (pipes, cables) 200 to a power and liquid coolant supply unit. The tubes and connecting cables are not shown in detail.

The piece 100 has a shell 110, which forms a handle connected to the tubes and cables 200, and a phototreatment head; the shell 110 houses a cartridge which is equipped with a controlled light source for emitting light of a given wavelength and according to a programmed and controlled emission, for example a pulsed emission, a flash emission, a succession of pulses according to a frequency and a succession of controlled pulses.

The light is emitted by the handpiece by way of a light guide 300 which connects the light source to the outside, forming an emission surface 301 which is to be brought up to the area of skin to be treated, or above it, depending on the nature of the treatment to be carried out. Where appropriate, the light guide 300 also acts as a filter, allowing only radiation of a precise wavelength to pass through.

According to FIG. 3, the shell 110 is composed of two substantially symmetrical parts 110a, 110b which meet along the vertical mid-plane VI VI of the handpiece (by convention, that direction of the vertical plane is the direction of the sheet of the drawing of FIG. 2), leaving on the top a zone which receives a cap 120 and corresponds at least in part to the site of the cartridge. The two parts 110a, b of the shell 110 are assembled by means of transverse screw connections or screw points 112, and the cap 120 is fitted to the opening by sliding and locks in the closed position. Locking is effected by a hook integrated into the cap 120, which is released by operation of a push-button 121 visible on the top of the cap.

The sectional view of FIG. 4 through the plane of symmetry shows more particularly the structure of the shell and of the site of the cartridge 400, as well as of the light guide 300. This view of the half-shell 110b along the plane of symmetry VI VI is a section showing the two parts of the shell, which fit together along their joining plane by an edge-overlapping connection, which may be of the tongue and groove type. The hook 122, combined with the push-button 121, is articulated with the cover in order to engage in a catch member 111 in the homologous position on the inside of the shell. The two parts of the shell 110 are screwed together by screws 112 substantially perpendicular to the mid-plane VI VI, as can be seen in FIGS. 5A, 5C. For the screw points 112, one of the parts 110a, b of the shell 110 comprises reinforced orifices 113 for the passage of the screws 112, and the other part comprises screw bores 114 in which the screws 112 cut their own threads or which include overmoulded screw nuts of the material of the shell. The screw points are distributed at the end of the handle, in the middle thereof and in the region of the site of the cartridge 400 and of the light guide 300, beneath the cap 120. The site of the cartridge located above the light guide 300 is produced as shown in FIGS. 4, 5A, B, C, D, 6, 7.

According to FIG. 4, the site of the cartridge 400 located above the light guide 300 is formed both by lateral slides 115 (FIGS. 6 and 7) in the two parts 110a, b of the shell 110 and at the end, on the handle side, by a base 500 fitted by an interference fit, optionally supplemented by screwing, into housings in the two parts 110a, b of the shell 110 at the time of their assembly. To that end, the two parts 110a, b comprise ribs 116. The base 500 is itself connected to the liquid coolant inlet/outlet pipes and to the power supply cable for the light source and, where appropriate, to a signal transmission cable which supplies a display surface such as a screen. The display surface (not shown), which is provided on the top of the handpiece, displays, for example, the operating state and signals from sensors integrated into the handpiece, such as a temperature sensor, a contact sensor or a photosensor for detecting the operating temperature, the presence of the light guide 300 or the presence and/or nature of the surface located in front of the light guide. The display on the handle indicates the chosen programme and other features reproducing, for reasons of convenience, at least in part the display produced on the central unit.

The information to be exchanged between the handle and the device can also be signals provided by sensors (not shown) integrated into the handpiece, such as temperature sensors controlling the liquid coolant circuit or safety circuit sensors or sensors for connection of the cartridge 400.

The sectional view of FIG. 4 and the side view of the half-shell 110b of FIG. 6 show more particularly the site of the cartridge and the lateral rails 115 for sliding the cartridge into its site, by a straight movement to the left according to the orientation of FIG. 6, until the connection and insertion elements of the cartridge 400 are connected to those of the base 500.

The side view of the half-shell 110b according to FIG. 6 shows the reinforcing ribs 116 for fixing of the base 500, and the ribs 117 forming a cable clamp at the outlet of the handle.

FIGS. 5A to 5D show more particularly the structure of the shell in different transverse cutting planes.

FIG. 5A is a sectional view in the region of the screw points at the end of the handle. This view shows the screws 112 housed in the screw bores 114 of the part 110b after passing through the reinforced orifice 113 of the shell part 110a.

FIG. 5B shows the section of the cartridge 400 above the optical guide 300 with the rails 115 of the shell 110 cooperating with the casing of the cartridge 400.

FIG. 5C is a sectional view of the front of the cartridge 400, showing the central housing of the light source 401 bordered on each side by the liquid coolant channel 402.

In the region of this section, there is also a screwed connection with a screw 112 housed in a screw bore 114 by passing through a reinforced orifice 113 in each of the parts 110a, 110b of the shell.

Finally, FIG. 5D is a sectional view of the front end of the shell 110 and of the cap 120, in the region of the support elements 122 in the form of ribs of the cap 120.

The cap 120 shown in FIGS. 7 and 8 has a shape complementary to that of the opening around the site of the cartridge, formed by assembly of the two halves of the shell. The cap 120 has a lower edge with a return portion 123 for cooperation with the additional lateral rails 118 located at the base of the site of the cartridge, on each side. Accordingly, and as shown in FIG. 3, the cap 120, fitted by a sliding movement, secures the cartridge 400 by its stop 124. At the front, the cap 120 is retained by a nose 119 of the shell 110 and, at the back, it is retained by its hook 122 in the catch member 111. Since the cap 120 is thus fitted and locked, the cartridge 400 is accordingly locked. In order to withdraw the cartridge 400, it is first necessary to unlock the cap 120 and then slide it in order to withdraw it. The cartridge 400 can then be withdrawn from its site and replaced by a cartridge having different optical characteristics.

FIG. 8 shows the shape of the cap 120.

The base 500 and the cartridge 400 are shown in greater detail in FIGS. 9 and 10A, B, C.

According to FIG. 9, the base 500 is constituted by a plate 510 which slides into the transverse housing formed in each of the halves 110a, b of the shell 110 by ribs. The housing is formed when the shell is assembled. The plate 510 of the base comprises screw orifices 511 which additionally allow the base to be screwed onto the two parts of the shell.

The front face of the base 500 is provided with a connector for the electronic/electrical connections 520 and two nozzles 530 for receiving connecting pieces of the liquid coolant circuit of the cartridge 400.

The cartridge 400, shown in the position aligned with the base 500 for engagement therewith, is constituted by a flat elongate casing 410 which is terminated on one side by an assembly plate 420 for connection to the base 500. The assembly plate 420 comprises male/female elements 421 corresponding to those 520, 530 of the base 500, namely: a complementary socket or connector 421 for cooperation with the connector 520 of the base, and two connecting pieces 422 with seals which are introduced into the two liquid coolant connecting nozzles 530.

The cartridge 400 is formed by a casing in two parts, a lower part 430 and an upper part 440. Once assembled, the two parts have a common contour, which comprises two grip zones 450 of dished shape provided with ribs or bumps which assist with holding of the cartridge 400 and its removal or insertion in the base 500. The two grip zones 450 have a considerable height, extending beyond the base form of the housing 410 to constitute grip surfaces providing a good grip for the fingers.

In the region of the lower part 430, the sides of the casing of the cartridge comprise two guide ribs 460 which are to cooperate with the lateral rails 115 of the shell 110.

The base 500 or the shell can also comprise a detection means for detecting the type of cartridge used and authorising only the operating programmes applied by the device and compatible with the type of light source or light guide used.

The top of the casing 410 is strengthened by a rib 411.

FIG. 10A is a top view of the cartridge 400 showing its window 431 behind which the controlled light source is located.

The side view of FIG. 10B shows very particularly the guide ribs 460 and the grip zones 450.

This side view shows the joining plane of the two parts 430, 440 of the casing, which is substantially parallel to the plane of the site of the cartridge in the shell.

The bottom view of FIG. 10C, like FIG. 10A, shows the general shape of the cartridge.

According to a variant which is not shown, the handpiece comprises cells for analysing the pigmentation of the skin in order to analyse the skin prior to any treatment, as a safety measure. This also allows the operator to choose the treatment parameters in terms of the safety and effectiveness of the treatment.

The shell 110, its cap 120 and the cartridge 400 and the base 500 are, preferably, pieces produced from plastics material by injection moulding.

FIGS. 11 to 14 show a variant of a handpiece 100A. For the description thereof, the same reference numerals will be used as for the first embodiment, those reference numerals being supplemented, as appropriate, by the suffix A for the modifications affected by the variant.

Thus, according to FIG. 11, the variant of the handpiece 100A is composed of a shell 110A which houses, in a removable manner, a cartridge and a light guide 300 shown in part as protruding from the bottom of the handpiece. At the site of the cartridge 400, the top of the cap 120A of the handpiece comprises a slightly projecting part 126A which is provided with a plurality of ventilation orifices 127A and, in the prolongation of those aeration orifices according to FIG. 11, the two sides of the shell 110A of the handpiece, above the light guide 300, there are ventilation slots 128A. The orifices 127A on the top and the ventilation slots 128A permit the creation of a passage of air, forced by a fan 140A integrated into the handpiece 110A.

FIG. 12 shows in greater detail the cap 120A of the handpiece 100A with the air inlet orifices 127A on the top and the bulging portion 126A which is to accommodate the excess thickness caused by the housing receiving the fan.

The rear edge 128A of the cap 120A comprises two pins 130A for the power supply to the fan. The two pins engage in contact sockets carried by the shell 110A in the region of its opening receiving the cap 120A.

The partial longitudinal sectional view according to FIG. 13 shows the position of the fan 131A inside the cap 120A of the handpiece. The fan is located exactly above the cartridge 400, in the region of its centre, which is the hottest part of the cartridge. The fan 131A is fitted or clipped into a housing defined by tabs 132A moulded with the cap. The casing of the fan 131A is thus fitted into the cap and held therein.

Power is supplied to the fan by the two pins 130A mentioned above, which are not shown in FIG. 13.

FIG. 13 also shows, in a sketched manner, the ventilation slots 128A on the two sides of the shell 110A in the region of the cartridge 400, slightly beneath the cartridge so that the flow of air drawn in by the fan 131A through the orifices 127A in the top of the cap, in the region of its site, also passes over the sides of the cartridge 400 before emerging through the slots 128A in the shell 110A.

FIG. 14 shows, in greater detail, the installation of the fan 131A in the wall of the top of the cap 120A. The fan is fixed in partitions forming the tabs 132A into which it is clipped.

Power is supplied to the fan by way of the two pins 130A carried by a support 133A. The pins are connected to the fan by cables (not shown). They are to engage in contact housings carried by the shell 110A.

The pins 130A are located next to the hook 122A which locks the cap 120 to the shell 110A. The other elements of the cap 120A, which are identical to those of the first embodiment, bear the same reference numerals with the addition of the suffix A, and their description will not be repeated.

The control circuit for the fan 131A has not been shown. It supplies the appropriate power to the fan 131A so that it delivers as required. The control circuit comprises a temperature sensor housed in the shell 110A for detecting the temperature of the closed enclosure, constituted by the shell 110A and the cap 120A around the cartridge 400. The temperature signal is compared with a recorded limit temperature. Depending on the result of the comparison, the fan 131A will be operated at one of three speeds corresponding to three different flow rates. Control of the motor of the fan 131A is effected by controlling the voltage level supplied to the motor. Finally, a safety feature is provided for an extreme situation in which it would prove impossible to lower the temperature below a fixed threshold and, in that extreme case, operation of the device would be stopped.

NOMENCLATURE 100, 100A handpiece
110, 110A shell
110a, 110b parts of the shell
111 catch member
112 screw connection/screw/screw point
113 reinforced orifice
114 screw bore
115 lateral slide
116 rib
117 rib
118 additional lateral rails
119 nose
120, 120A cap
121, 121A push-button
122, 122A hook
123 return portion
124 stop
126A projecting part
127A ventilation orifices
128A ventilation slots
129A rear edge
130A pins
131A fan
132A tab
133A support for the pins
200 electrical fluidic connections
300 light guide
301 emission surface
400 cartridge
401 light source
402 liquid coolant channel
410 base of the casing
411 guide rib
421 socket or connector
422 connecting piece with seals
430 lower part
431 window
440 upper part
450 grip zone
460 guide rib
500 base
510 plate
511 screw orifice
520 electronic/electrical connections
530 nozzle

The invention claimed is:

1. Handpiece for a cosmetic, medical/therapeutic skin phototreatment device, which handpiece is connected to a power source and liquid coolant supply unit by a cable and tube connection in the device, the handpiece comprising:
a shell which houses, in a removable manner, a cartridge with a window having a light source and its cooling circuit, a cap that mates with the shell and encloses the cartridge in the shell at a seating location in the shell,
a light guide housed within the shell and partially extending therefrom, the light guide being connected to the light source by the window of the cartridge and having a light outlet surface to be applied to or above the surface of the skin to be treated,
characterised in that
the inner portions of the shell adjacent the portion of the cartridge above the portion of the light guide housed within the shell defining a base for carrying power and coolant supply conduits for the cartridge and defining a guide surface having at least one end which corresponds to the base and at least two sides which define lateral guide rails around the light guide, and
the cartridge being in the form of a planar casing, one end of which carries a transverse assembly plate provided with connection members for mating with the base, and the sides of which comprise guide ribs for cooperating with the lateral rails and positioning the cartridge and guiding it for translational movement towards the seating location for insertion and for connection with the supply conduits, and for keeping it connected to the supply conduits when in the seating location.

2. Handpiece according to claim 1, characterised in that at the seating location, the shell comprises additional rails parallel to the lateral guide rails and a clip-fit element, and the cap comprises guide members for sliding in the additional rails, as well as a complementary clip-fit element for cooperating with the clip-fit element of the shell when the cap is in mating engagement with the shell.

3. Handpiece according to claim 1, characterised in that the casing of the cartridge comprises two lateral grip zones which allow the casing to be grasped by hand or withdrawn and inserted by a sliding movement of its ribs in the rails.

4. Handpiece according to claim 1, characterised in that the casing of the cartridge is formed by a first part and a second part which house the light source and a liquid coolant circuit to cool the light source,
one of the parts has a window in which the light source appears in order to transmit its light flux,
the two parts being assembled along a joining plane which is substantially parallel to the plane of the seating location,
one part carrying the ribs, and an assembly plate at one end.

5. Handpiece according to claim 1, characterised in that the shell forming a handle and a head housing the cartridge comprises two parts, which meet substantially in a mid-plane of the shell when the two parts are assembled together, as well as the cap above the seating location and a housing for receiving the base for connection of the cartridge.

6. Handpiece according to claim 1, characterised in that
the cap comprises a fan in an upper wall thereof, and is provided with ventilation orifices above the seating location,
the shell having in its lateral walls, on either side of the cartridge, ventilation slots for the exit of air,
an air passage path being formed between the ventilation orifices in the cap, through the fan and the top of the cartridge and then dividing towards the sides of the cartridge and emerging through the ventilation slots of the shell.

7. Handpiece according to claim 6, characterised in that the cap comprises two pins for supplying electric power to the fan, which pins engage in sockets in the shell.

8. Handpiece according to claim 6, characterised in that the fan is held in position by retaining tabs moulded in one piece with the cap.

9. Handpiece according to claim 1, characterised by a control circuit for controlling operating speed and air flow rate of the fan, the control circuit being connected to a temperature sensor associated with the interior of the shell in order to control the operation of the fan as a function of temperature in the interior of the shell.

* * * * *